(12) United States Patent
Schwager et al.

(10) Patent No.: US 10,166,131 B2
(45) Date of Patent: *Jan. 1, 2019

(54) PROCESS FOR LOADING A STENT ONTO A STENT DELIVERY SYSTEM

(71) Applicant: ABBOTT LABORATORIES VASCULAR ENTERPRISES LIMITED, Dublin (IE)

(72) Inventors: Michael Schwager, Winterhur (CH); Martin Frei, Schaffhausen (CH); Suk-Woo Ha, Marthalen (CH)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 257 days.

This patent is subject to a terminal disclaimer.

(21) Appl. No.: 15/058,407

(22) Filed: Mar. 2, 2016

(65) Prior Publication Data

US 2016/0175130 A1 Jun. 23, 2016

Related U.S. Application Data

(60) Continuation of application No. 11/064,692, filed on Feb. 23, 2005, now Pat. No. 9,295,570, which is a
(Continued)

(51) Int. Cl.
*A61F 2/958* (2013.01)
*A61F 2/91* (2013.01)
(Continued)

(52) U.S. Cl.
CPC ............... *A61F 2/958* (2013.01); *A61F 2/91* (2013.01); *A61F 2/915* (2013.01);
(Continued)

(58) Field of Classification Search
CPC .. A61F 2/95; A61F 2/954; A61F 2/958; A61F 2/97; A61F 2002/9505;
(Continued)

(56) References Cited

U.S. PATENT DOCUMENTS 3,687,135 A 8/1972 Stroganov et al.
3,839,743 A 10/1974 Schwarcz
(Continued)

FOREIGN PATENT DOCUMENTS

DE 44 07 079 9/1994
DE 195 09 464 6/1996
(Continued)

OTHER PUBLICATIONS

U.S. Appl. No. 13/502,084, filed Oct. 29, 2010, Grandt.
(Continued)

*Primary Examiner* — Elizabeth Houston
*Assistant Examiner* — Lindsey Bachman
(74) *Attorney, Agent, or Firm* — Baker Botts L.L.P.

(57) ABSTRACT

Stent delivery system having a contracted delivery configuration and an expanded deployed configuration is provided. The stent delivery system includes a stent having a plurality of expandable elements and a plurality of interstices disposed between adjacent expandable elements, and a delivery catheter having an inflatable balloon including creases extending non-uniformly within the interstices of the stent in the contracted delivery configuration. Each crease defines a maximum radial height within a corresponding interstice, and the maximum radial heights of the creases vary. A method for stenting at a target site within a patient's vessel including providing a stent delivery system is also provided.

17 Claims, 7 Drawing Sheets

Related U.S. Application Data division of application No. 09/957,216, filed on Sep. 19, 2001, now Pat. No. 6,863,683.

(51) Int. Cl.
*A61F 2/915* (2013.01)
*A61M 25/10* (2013.01)
*A61F 2/95* (2013.01)

(52) U.S. Cl.
CPC .............. *A61F 2002/91533* (2013.01); *A61F 2002/91558* (2013.01); *A61F 2002/9522* (2013.01); *A61F 2002/9583* (2013.01); *A61F 2310/00011* (2013.01); *A61M 2025/1004* (2013.01); *Y10T 29/49927* (2015.01)

(58) Field of Classification Search
CPC ................ A61F 2002/9511–2002/9534; A61F 2002/9583; A61F 2002/9665
USPC ....................................................... 623/1.11
See application file for complete search history.

(56) References Cited

U.S. PATENT DOCUMENTS

| | | |
|---|---|---|
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,990,151 A | 2/1991 | Wallsten |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,100,429 A | 3/1992 | Sinofsky et al. |
| 5,104,410 A | 4/1992 | Chowdhary |
| 5,108,417 A | 4/1992 | Sawyer |
| 5,112,457 A | 5/1992 | Marchant |
| 5,123,917 A | 6/1992 | Lee |
| 5,147,385 A | 9/1992 | Beck et al. |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,292,321 A * | 3/1994 | Lee ......................... A61B 17/22 606/198 |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,507,768 A | 4/1996 | Lau et al. |
| 5,514,154 A | 5/1996 | Lau et al. |
| 5,514,379 A | 5/1996 | Weissleder et al. |
| 5,527,337 A | 6/1996 | Stack et al. |
| 5,545,208 A | 8/1996 | Wolff et al. |
| 5,545,408 A | 8/1996 | Trigg et al. |
| 5,549,635 A | 8/1996 | Solar |
| 5,554,120 A | 9/1996 | Chen et al. |
| 5,556,413 A | 9/1996 | Lam |
| 5,569,295 A | 10/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A * | 2/1997 | Eury ......................... A61L 31/10 264/4.3 |
| 5,607,442 A | 3/1997 | Fischell et al. |
| 5,607,467 A | 3/1997 | Froix |
| 5,618,299 A | 4/1997 | Khosravi et al. |
| 5,628,784 A | 5/1997 | Strecker |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greif et al. |
| 5,667,796 A | 9/1997 | Otten |
| 5,670,558 A | 9/1997 | Onishi et al. |
| 5,690,644 A | 11/1997 | Yurek et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,393 A | 2/1998 | Lindenberg et al. |
| 5,716,981 A | 2/1998 | Hunter et al. |
| 5,725,549 A | 3/1998 | Lam |
| 5,726,297 A | 3/1998 | Gryaznov et al. |
| 5,728,068 A | 3/1998 | Leone et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |

(56) References Cited

U.S. PATENT DOCUMENTS

| | | |
|---|---|---|
| 5,756,457 A | 5/1998 | Wang et al. |
| 5,756,476 A | 5/1998 | Epstein et al. |
| 5,759,474 A | 6/1998 | Rupp et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,776,140 A | 7/1998 | Cottone |
| 5,780,807 A | 7/1998 | Saunders |
| 5,782,839 A | 7/1998 | Hart et al. |
| 5,792,144 A | 8/1998 | Fischell et al. |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,836,965 A * | 11/1998 | Jendersee ............... A61F 2/958 604/103.07 |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greif et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,860,966 A | 1/1999 | Tower |
| 5,865,814 A | 2/1999 | Tuch |
| 5,868,781 A | 2/1999 | Killion |
| 5,871,468 A | 2/1999 | Kramer et al. |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,893,852 A | 4/1999 | Morales |
| 5,897,955 A | 4/1999 | Drumheller |
| 5,906,759 A | 5/1999 | Richter |
| 5,913,871 A | 6/1999 | Werneth et al. |
| 5,914,182 A | 6/1999 | Drumheller |
| 5,916,870 A | 6/1999 | Lee et al. |
| 5,920,975 A | 7/1999 | Morales |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,181 A * | 11/1999 | Whelan ............... A61F 2/958 606/194 |
| 5,976,182 A | 11/1999 | Cox |
| 5,980,530 A | 11/1999 | Willard et al. |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,022,359 A | 2/2000 | Frantzen |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,063,092 A | 5/2000 | Shin |
| 6,066,156 A | 5/2000 | Yan |
| 6,071,266 A | 6/2000 | Kelley |
| 6,074,381 A | 6/2000 | Dinh et al. |
| 6,074,659 A | 6/2000 | Kunz et al. |
| 6,080,177 A | 6/2000 | Igaki et al. |
| 6,080,488 A | 6/2000 | Hostettler et al. |
| 6,082,990 A | 7/2000 | Jackson et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,106,530 A | 8/2000 | Harada |
| 6,107,416 A | 8/2000 | Patnaik et al. |
| 6,110,180 A | 8/2000 | Foreman et al. |
| 6,110,188 A | 8/2000 | Narciso, Jr. |
| 6,113,629 A | 9/2000 | Ken |
| 6,117,979 A | 9/2000 | Hendriks et al. |
| 6,120,522 A | 9/2000 | Vrba et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,141,855 A | 11/2000 | Morales |
| 6,150,630 A | 11/2000 | Perry et al. |
| 6,153,252 A | 11/2000 | Hossainy et al. |
| 6,159,227 A | 12/2000 | Di Caprio et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,013 B1 | 2/2001 | Stoltze et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Yianen et al. |
| 6,251,135 B1 | 6/2001 | Stinson et al. |
| 6,251,142 B1 | 6/2001 | Bernacca et al. |
| 6,264,683 B1 | 7/2001 | Stack et al. |
| 6,267,776 B1 | 7/2001 | O'Connell |
| 6,273,913 B1 | 8/2001 | Wright et al. |
| 6,280,412 B1 | 8/2001 | Pederson et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,296,655 B1 | 10/2001 | Gaudoin et al. |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,352,547 B1 | 3/2002 | Brown et al. |
| 6,375,660 B1 * | 4/2002 | Fischell ............... A61F 2/95 606/108 |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |

(56) References Cited

U.S. PATENT DOCUMENTS

| | | |
|---|---|---|
| 6,479,565 B1 | 11/2002 | Stanley |
| 6,481,262 B2 | 11/2002 | Ching et al. |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,510,722 B1 | 1/2003 | Ching et al. |
| 6,511,748 B1 | 1/2003 | Barrows |
| 6,517,559 B1 | 2/2003 | O'Connell |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,551,303 B1 | 4/2003 | Van Tassel et al. |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,579,305 B1 | 6/2003 | Lashinski |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessier |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,745,445 B2 | 6/2004 | Spilka |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,504 B2 | 7/2004 | Wang et al. |
| 6,764,505 B1 | 7/2004 | Hossainy et al. |
| 6,769,161 B2 | 8/2004 | Brown et al. |
| 6,818,063 B1 | 11/2004 | Kerrigan |
| 6,846,323 B2 | 1/2005 | Yip et al. |
| 6,863,683 B2 | 3/2005 | Schwager et al. |
| 7,008,446 B1 | 3/2006 | Amis et al. |
| 7,347,869 B2 | 3/2008 | Hojeibane et al. |
| 7,470,281 B2 | 12/2008 | Tedeschi |
| 7,563,400 B2 | 7/2009 | Wilson et al. |
| 7,722,663 B1 | 5/2010 | Austin |
| 7,731,740 B2 | 6/2010 | LaFont et al. |
| 7,763,198 B2 | 7/2010 | Knott et al. |
| 7,776,926 B1 | 8/2010 | Hossainy et al. |
| 7,947,207 B2 | 5/2011 | Mcniven et al. |
| 8,236,039 B2 | 8/2012 | Mackiewicz |
| 8,309,023 B2 | 11/2012 | Ramzipoor |
| 8,333,000 B2 | 12/2012 | Huang et al. |
| 2001/0001128 A1 | 5/2001 | Holman et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0007207 A1 | 1/2002 | Shin et al. |
| 2002/0035774 A1 | 3/2002 | Austin |
| 2002/0062148 A1 | 5/2002 | Hart |
| 2002/0065553 A1 | 5/2002 | Weber |
| 2002/0068967 A1 | 6/2002 | Drasler et al. |
| 2002/0111590 A1 | 8/2002 | Davila et al. |
| 2002/0116050 A1 | 8/2002 | Kocur |
| 2002/0138127 A1 | 9/2002 | Stiger et al. |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0040772 A1 | 2/2003 | Hyodoh et al. |
| 2003/0055482 A1 | 3/2003 | Schwager et al. |
| 2003/0056360 A1 | 3/2003 | Brown et al. |
| 2003/0078538 A1 | 4/2003 | Neale et al. |
| 2003/0093107 A1 | 5/2003 | Parsonage et al. |
| 2003/0097172 A1 | 5/2003 | Shalev et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208227 A1 | 11/2003 | Thomas |
| 2003/0208259 A1 | 11/2003 | Penhasi |
| 2003/0209835 A1 | 11/2003 | Chun et al. |
| 2003/0212450 A1 | 11/2003 | Schlick |
| 2003/0226833 A1 | 12/2003 | Shapovalov et al. |
| 2003/0236565 A1 | 12/2003 | Fifer |
| 2004/0073155 A1 | 4/2004 | Laufer et al. |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Weber |
| 2004/0133263 A1 | 7/2004 | Dusbabek et al. |
| 2004/0138731 A1 | 7/2004 | Johnson |
| 2004/0143317 A1 | 7/2004 | Stinson et al. |
| 2004/0167610 A1 | 8/2004 | Fleming, III |
| 2004/0199246 A1 | 10/2004 | Chu et al. |
| 2005/0096735 A1 | 5/2005 | Hojeibane et al. |
| 2005/0118344 A1 | 6/2005 | Pacetti |
| 2005/0143752 A1 | 6/2005 | Schwager et al. |
| 2005/0154450 A1 | 7/2005 | Larson et al. |
| 2005/0183259 A1 | 8/2005 | Eidenschink et al. |
| 2005/0203606 A1 | 9/2005 | Vancamp |
| 2005/0267408 A1 | 12/2005 | Grandt et al. |
| 2005/0283962 A1 | 12/2005 | Boudjemline |
| 2006/0004328 A1 | 1/2006 | Joergensen et al. |
| 2006/0020285 A1 | 1/2006 | Niermann |
| 2006/0030923 A1 | 2/2006 | Gunderson |
| 2006/0041271 A1 | 2/2006 | Bosma et al. |
| 2006/0047336 A1 | 3/2006 | Gale et al. |
| 2006/0058863 A1 | 3/2006 | LaFont et al. |
| 2006/0100694 A1 | 5/2006 | Globerman |
| 2006/0229712 A1 | 10/2006 | Wilson et al. |
| 2006/0287708 A1 | 12/2006 | Ricci et al. |
| 2006/0288561 A1 | 12/2006 | Roach et al. |
| 2007/0006441 A1 | 1/2007 | Mcniven et al. |
| 2007/0204455 A1 | 9/2007 | Boyd et al. |
| 2007/0208370 A1 | 9/2007 | Hauser et al. |
| 2007/0255388 A1 | 11/2007 | Rudakov et al. |
| 2007/0289117 A1 | 12/2007 | Huang et al. |
| 2008/0097570 A1 | 4/2008 | Thornton et al. |
| 2008/0208118 A1 | 8/2008 | Goldman |
| 2009/0076448 A1 | 3/2009 | Consigny et al. |
| 2009/0105747 A1 | 4/2009 | Chanduszko et al. |
| 2009/0187210 A1 | 7/2009 | Mackiewicz |
| 2009/0187211 A1 | 7/2009 | Mackiewicz |
| 2009/0292347 A1 | 11/2009 | Asmus et al. |
| 2010/0152765 A1 | 6/2010 | Haley |
| 2011/0106234 A1 | 5/2011 | Grandt |
| 2011/0257675 A1 | 10/2011 | Mackiewicz |
| 2012/0035704 A1 | 2/2012 | Grandt |
| 2012/0259402 A1 | 10/2012 | Grandt |
| 2012/0283814 A1 | 11/2012 | Huang et al. |
| 2013/0239396 A1 | 9/2013 | Schwager et al. |
| 2013/0269168 A1 | 10/2013 | Huang et al. |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |

(56) References Cited

FOREIGN PATENT DOCUMENTS

| | | |
|---|---|---|
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 716 836 | 6/1996 |
| EP | 0 787 020 | 8/1997 |
| EP | 0 935 952 | 8/1999 |
| EP | 0 970 711 | 1/2000 |
| EP | 1 000 591 | 5/2000 |
| EP | 1 226 798 | 7/2002 |
| EP | 1 295 570 | 3/2003 |
| EP | 1 637 177 | 3/2006 |
| EP | 2 029 052 | 3/2009 |
| EP | 2 196 174 | 6/2010 |
| EP | 2 322 118 | 5/2011 |
| GB | 2 247 696 | 3/1992 |
| WO | WO 1989/003232 | 4/1989 |
| WO | WO 1990/001969 | 3/1990 |
| WO | WO 1990/004982 | 5/1990 |
| WO | WO 1990/006094 | 6/1990 |
| WO | WO 1990/117744 | 11/1991 |
| WO | WO 1991/117789 | 11/1991 |
| WO | WO 1992/010218 | 6/1992 |
| WO | WO 1993/006792 | 4/1993 |
| WO | WO 1994/021196 | 9/1994 |
| WO | WO 1995/029647 | 11/1995 |
| WO | WO 1998/004415 | 2/1998 |
| WO | WO 1999/003515 | 1/1999 |
| WO | WO 1999/016382 | 4/1999 |
| WO | WO 1999/016386 | 4/1999 |
| WO | WO 1999/042147 | 8/1999 |
| WO | WO 1999/055255 | 11/1999 |
| WO | WO 2000/012147 | 3/2000 |
| WO | WO 2000/064506 | 11/2000 |
| WO | WO 00/78249 | 12/2000 |
| WO | WO 01/05462 | 1/2001 |
| WO | WO 2001/001890 | 1/2001 |
| WO | WO 01/21110 | 3/2001 |
| WO | WO 2002/102283 | 12/2002 |
| WO | WO 2004/023985 | 3/2004 |
| WO | WO 2004/047681 | 6/2004 |
| WO | WO 2005/053937 | 6/2005 |
| WO | WO 2006/110861 | 10/2006 |
| WO | WO 07/061927 | 5/2007 |
| WO | WO 08/024491 | 2/2008 |
| WO | WO 08/024621 | 2/2008 |
| WO | WO 2008/033621 | 3/2008 |
| WO | WO 09/066330 | 5/2009 |
| WO | WO 09/086205 | 7/2009 |
| WO | WO 2010/066446 | 6/2010 |
| WO | WO 2011/050979 | 5/2011 |

OTHER PUBLICATIONS

U.S. Appl. No. 61/016,266, filed Dec. 21, 2007, Mackiewicz.
U.S. Appl. No. 61/138,455, filed Dec. 17, 2008, Haley.
U.S. Appl. No. 09/957,216 (U.S. Pat. No. 6,863,683), filed Sep. 19, 2001 (Mar. 8, 2005).
U.S. Appl. No. 11/064,692 (U.S. Pat. No. 9,295,570), filed Feb. 23, 2005 (Mar. 29, 2016).
U.S. Appl. No. 11/471,375 (U.S. Pat. No. 8,333,000), filed Jun. 19, 2006 (Dec. 18, 2012).
U.S. Appl. No. 12/338,980 (U.S. Pat. No. 8,236,039), filed Dec. 18, 2008 (Aug. 7, 2012).
U.S. Appl. No. 12/338,981 (US 2009/0187211), filed Dec. 18, 2008 (Jul. 23, 2009) (Abandoned).
U.S. Appl. No. 12/537,097 (US 2010/0152765), filed Aug. 6, 2009 (Jun. 17, 2010) (Abandoned).
U.S. Appl. No. 12/609,513, (US 2011/0106234), filed Oct. 30, 2009 (May 5, 2011) (Abandoned).
U.S. Appl. No. 13/133,930 (U.S. Pat. No. 8,591,565), filed Oct. 20, 2011 (Nov. 26, 2013).
U.S. Appl. No. 13/151,893 (US 2011/0257675), filed Jun. 2, 2011 (Oct. 20, 2011) (Abandoned).
U.S. Appl. No. 13/551,538 (U.S. Pat. No. 8,925,177), filed Jul. 17, 2012 (Jan. 6, 2015).
U.S. Appl. No. 13/779,636 (U.S. Pat. No. 9,259,341), filed Feb. 27, 2013 (Feb. 16, 2016).
U.S. Appl. No. 13/779,683 (US 2013/0239396), filed Feb. 27, 2013 (Sep. 19, 2013).
U.S. Appl. No. 14/552,066 (US 2015/0074975), filed Nov. 24, 2014 (Mar. 19, 2015).
U.S. Appl. No. 09/957,216, Aug. 4, 2003 Response to Restriction Requirement.
U.S. Appl. No. 09/957,216, Jun. 10, 2003 Restriction Requirement.
U.S. Appl. No. 09/957,216, Sep. 26, 2003 Non-Final Office Action.
U.S. Appl. No. 09/957,216, Mar. 8, 2004 Response to Non-Final Office Action.
U.S. Appl. No. 09/957,216, Jun. 14, 2004 Non-Final Office Action.
U.S. Appl. No. 09/957,216, Sep. 17, 2004 Response to Non-Final Office Action.
U.S. Appl. No. 09/957,216, Nov. 4, 2004 Notice of Allowance.
U.S. Appl. No. 09/957,216, Jan. 31, 2005 Issue Fee payment.
U.S. Appl. No. 11/064,692, Feb. 19, 2016 Issue Fee Payment.
U.S. Appl. No. 11/064,692, Nov. 19, 2015 Notice of Allowance.
U.S. Appl. No. 11/064,692, Aug. 3, 2015 Response to Non-Final Office Action.
U.S. Appl. No. 11/064,692, Apr. 1, 2015 Non-Final Office Action.
U.S. Appl. No. 11/064,692, Nov. 24, 2014 Amendment and Request for Continued Examination (RCE).
U.S. Appl. No. 11/064,692, Aug. 26, 2014 Final Office Action.
U.S. Appl. No. 11/064,692, Jul. 25, 2014 Response to Non-Final Office Action.
U.S. Appl. No. 11/064,692, Feb. 25, 2014 Non-Final Office Action.
U.S. Appl. No. 11/064,692, Jan. 15, 2014 Response to Non-Final Office Action.
U.S. Appl. No. 11/064,692, Jan. 7, 2014 Amendment and Request for Continued Examination (RCE).
U.S. Appl. No. 11/064,692, Oct. 2, 2013 Final Office Action.
U.S. Appl. No. 11/064,692, Sep. 10, 2013 Response to Non-Final Office Action.
U.S. Appl. No. 11/064,692, May 10, 2013 Non-Final Office Action.
U.S. Appl. No. 11/064,692, Nov. 2, 2011 Amendment and Request for Continued Examination (RCE).
U.S. Appl. No. 11/064,692, Aug. 2, 2011 Final Office Action.
U.S. Appl. No. 11/064,692, Jun. 29, 2011 Response to Non-Final Office Action.
U.S. Appl. No. 11/064,692, Mar. 29, 2011 Non-Final Office Action.
U.S. Appl. No. 11/064,692, Feb. 23, 2010 Amendment and Request for Continued Examination (RCE).
U.S. Appl. No. 11/064,692, Nov. 23, 2009 Final Office Action.
U.S. Appl. No. 11/064,692, Jul. 31, 2009 Response to Non-Final Office Action.
U.S. Appl. No. 11/064,692, Mar. 31, 2009 Non-Final Office Action.
U.S. Appl. No. 11/064,692, Feb. 17, 2009 Amendment and Request for Continued Examination (RCE).
U.S. Appl. No. 11/064,692, Oct. 14, 2008 Final Office Action.
U.S. Appl. No. 11/064,692, Jul. 21, 2008 Response to Non-Final Office Action.
U.S. Appl. No. 11/064,692, Feb. 21, 2008 Non-Final Office Action.
U.S. Appl. No. 11/471,375, Nov. 14, 2012 Issue Fee payment.
U.S. Appl. No. 11/471,375, Aug. 17, 2012 Notice of Allowance.
U.S. Appl. No. 11/471,375, Jun. 12, 2012 Response to Final Office Action.
U.S. Appl. No. 11/471,375, Apr. 13, 2012 Final Office Action.
U.S. Appl. No. 11/471,375, Mar. 8, 2012 Response to Non-Final Office Action.
U.S. Appl. No. 11/471,375, Dec. 8, 2011 Non-Final Office Action.
U.S. Appl. No. 11/471,375, Jun. 16, 2011 Response to Non-Final Office Action.
U.S. Appl. No. 11/471,375, Mar. 16, 2011 Non-Final Office Action.

(56) References Cited

OTHER PUBLICATIONS

U.S. Appl. No. 11/471,375, Jan. 18, 2011 Amendment and Request for Continued Examination (RCE).
U.S. Appl. No. 11/471,375, Sep. 15, 2010 Final Office Action.
U.S. Appl. No. 11/471,375, Aug. 20, 2010 Response to Non-Final Office Action.
U.S. Appl. No. 11/471,375, Aug. 5, 2010 Non-Final Office Action.
U.S. Appl. No. 11/471,375, Mar. 29, 2010 Response to Non-Final Office Action.
U.S. Appl. No. 11/471,375, Feb. 2, 2010 Non-Final Office Action.
U.S. Appl. No. 11/471,375, Oct. 6, 2009 Response to Non-Final Office Action.
U.S. Appl. No. 11/471,375, Jul. 6, 2009 Non-Final Office Action.
U.S. Appl. No. 12/338,980, Sep. 1, 2010 Response to Restriction Requirement.
U.S. Appl. No. 12/338,980, Aug. 2, 2010 Restriction Requirement Filed.
U.S. Appl. No. 12/338,980, Jan. 26, 2011 Response to Non-Final Office Action.
U.S. Appl. No. 12/338,980, Oct. 27, 2010 Non-Final Office Action.
U.S. Appl. No. 12/338,980, Mar. 1, 2011 Final Office Action.
U.S. Appl. No. 12/338,980, Jun. 30, 2011 Amendment and Request for Continued Examination (RCE).
U.S. Appl. No. 12/338,980, Apr. 3, 2012 Notice of Allowance.
U.S. Appl. No. 12/338,980, May 9, 2012 Request for Continued Examination (RCE).
U.S. Appl. No. 12/338,980, May 25, 2012 Notice of Allowance.
U.S. Appl. No. 12/338,980, Jun. 29, 2012 Issue Fee Payment.
U.S. Appl. No. 12/338,981, Jan. 26, 2011 Response to Non-Final Office Action.
U.S. Appl. No. 12/338,981, Mar. 2, 2011 Final Office Action.
U.S. Appl. No. 12/338,981, Oct. 27, 2010 Non-Final Office Action.
U.S. Appl. No. 12/338,981, Aug. 2, 2010 Restriction Requirement Filed.
U.S. Appl. No. 12/338,981, Sep. 1, 2010 Response to Restriction Requirement.
U.S. Appl. No. 12/338,981, Sep. 21, 2011 Notice of Abandonment.
U.S. Appl. No. 12/537,097, Jun. 27, 2012 Non-Final Office Action.
U.S. Appl. No. 12/537,097, Dec. 15, 2011 Restriction Requirement Filed.
U.S. Appl. No. 12/537,097, Jan. 12, 2012 Response to Restriction Requirement.
U.S. Appl. No. 12/537,097, Feb. 3, 2012 Non-Final Office Action.
U.S. Appl. No. 12/537,097, Feb. 14, 2012 Response to Non-Final Office Action.
U.S. Appl. No. 12/537,097, Feb. 1, 2013 Notice of Abandonment.
U.S. Appl. No. 12/609,513, Feb. 1, 2013 Final Office Action.
U.S. Appl. No. 12/609,513, Apr. 29, 2013 Amendment and Request for Continued Examination (RCE).
U.S. Appl. No. 12/609,513, Jul. 15, 2013 Applicant Initiated Interview Summary.
U.S. Appl. No. 12/609,513, Aug. 24, 2012 Non-Final Office Action.
U.S. Appl. No. 12/609,513, Mar. 12, 2012 Non-Final Office Action.
U.S. Appl. No. 12/609,513, Jun. 12, 2012 Response to Non-Final Office Action.
U.S. Appl. No. 12/609,513, Oct. 25, 2012 Applicant Initiated Interview Summary.
U.S. Appl. No. 12/609,513, Nov. 26, 2012 Response to Non-Final Office Action.
U.S. Appl. No. 12/609,513, Jul. 7, 2014 Non-Final Office Action.
U.S. Appl. No. 12/609,513, Feb. 27, 2015 Notice of Abandonment.
U.S. Appl. No. 13/133,930, Oct. 18, 2013 Issue Fee Payment.
U.S. Appl. No. 13/133,930, Jul. 18, 2013 Notice of Allowance.
U.S. Appl. No. 13/133,930, Jun. 27, 2013 Response to Non-Final Office Action.
U.S. Appl. No. 13/133,930, Mar. 27, 2013 Non-Final Office Action.
U.S. Appl. No. 13/151,893, Nov. 20, 2012 Notice of Abandonment.
U.S. Appl. No. 13/151,893, Apr. 3, 2012 Non-Final Office Action.
U.S. Appl. No. 13/151,893, Feb. 27, 2012 Response to Restriction Requirement.
U.S. Appl. No. 13/151,893, Jan. 27, 2012 Restriction Requirement Filed.
U.S. Appl. No. 13/551,538, Nov. 13, 2013 Final Office Action.
U.S. Appl. No. 13/551,538, Sep. 10, 2013 Response to Non-Final Office Action.
U.S. Appl. No. 13/551,538, Jun. 10, 2013 Non-Final Office Action.
U.S. Appl. No. 13/551,538, Jul. 15, 2014 Response to Non-Final Office Action.
U.S. Appl. No. 13/551,538, Apr. 15, 2014 Non-Final Office Action.
U.S. Appl. No. 13/551,538, Apr. 15, 2014 Applicant Initiated Interview Summary.
U.S. Appl. No. 13/551,538, Mar. 13, 2014 Amendment and Request for Continued Examination (RCE).
U.S. Appl. No. 13/551,538, Jun. 19, 2014 Applicant Initiated Interview Summary.
U.S. Appl. No. 13/551,538, Sep. 19, 2014 Notice of Allowance.
U.S. Appl. No. 13/551,538, Nov. 24, 2014 Issue Fee Payment.
U.S. Appl. No. 13/779,636, Jan. 5, 2016 Issue Fee Payment.
U.S. Appl. No. 13/779,636, Oct. 5, 2015 Notice of Allowance.
U.S. Appl. No. 13/779,636, Sep. 10, 2015 Applicant Initiated Interview Summary.
U.S. Appl. No. 13/779,636, Sep. 4, 2015 Amendment and Request for Continued Examination (RCE).
U.S. Appl. No. 13/779,636, Nov. 24, 2014 Amendment and Request for Continued Examination (RCE).
U.S. Appl. No. 13/779,636, Dec. 29, 2014 Non-Final Office Action.
U.S. Appl. No. 13/779,636, Mar. 30, 2015 Response to Non-Final Office Action.
U.S. Appl. No. 13/779,636, Jun. 5, 2015 Final Office Action.
U.S. Appl. No. 13/779,636, Aug. 22, 2014 Final Office Action.
U.S. Appl. No. 13/779,636, Aug. 22, 2014 Applicant Initiated Interview Summary.
U.S. Appl. No. 13/779,636, Jun. 18, 2014 Response to Non-Final Office Action.
U.S. Appl. No. 13/779,636, Dec. 18, 2013 Non-Final Office Action.
U.S. Appl. No. 13/779,683, Apr. 7, 2016 Final Office Action.
U.S. Appl. No. 13/779,683, Jan. 29, 2016 Applicant Initiated Interview Summary.
U.S. Appl. No. 13/779,683, Jan. 26, 2016 Response to Non-Final Office Action.
U.S. Appl. No. 13/779,683, Sep. 25, 2015 Non-Final Office Action.
U.S. Appl. No. 13/779,683, Jun. 27, 2014 Applicant Initiated Interview Summary.
U.S. Appl. No. 14/552,066, Apr. 27, 2016 Final Office Action.
U.S. Appl. No. 14/552,066, Feb. 1, 2016 Applicant Initiated Interview Summary.
U.S. Appl. No. 14/552,066, Jan. 29, 2016 Response to Non-Final Office Action.
U.S. Appl. No. 14/552,066, Jul. 29, 2015 Non-Final Office Action.
Anonymous, "Bioabsorbable stent mounted on a catheter having optical coherence tomography capabilities", Research Disclosure, pp. 1159-1162, (2004).
Ansari, "End-to-end tubal anastomosis using an absorbable stent", Fertility and Sterility, 32(2):197-201 (1979).
Ansari, "Tubal Reanastomosis Using Absorbable Stent", International Journal of Fertility, 23(4):242-243 (1978).
Bull, "Parylene Coating for Medical Applications", Medical Product Manufacturing News, 18:1 (1993).
Casper, et al., "Fiber-Reinforced Absorbable Composite for Orthopedic Surgery", Polymeric Materials Science and Engineering, 53:497-501 (1985).
Detweiler, et al., "Gastrointestinal Sutureless Anastomosis Using Fibrin Glue: Reinforcement of the Sliding Absorbable Intraluminal Nontoxic Stent and Development of a Stent Placement Device", Journal of Investigative Surgery, 9(2):111-130 (1996).
Detweiler, et al., "Sliding, Absorbable, Reinforced Ring and an Axially Driven Stent Placement Device for Sutureless Fibrin Glue Gastrointestinal Anastomisis", Journal of Investigative Surgery, 9(6):495-504 (1996).
Detweiler, et al., "Sutureless Anastomosis of the Small Intestine and the Colon in Pigs Using an Absorbable Intraluminal Stent and Fibrin Glue", Journal of Investigative Surgery, 8(2):129-140 (1995).

(56) References Cited

OTHER PUBLICATIONS

Detweiler, et al., "Sutureless Cholecystojejunostomu in Pigs Using an Absorbable Intraluminal Stent and Fibrin Glue", Journal of Investigative Surgery, 9(1):13-26 (1996).
Devanathan, et al., "Polymeric Conformal Coatings for Implantable Electronic Devices", IEEE Transactions on Biomedical Engineering, BME-27(11):671-675 (1980).
Elbert, et al., "Conjugate Addition Reactions Combined with Free-Radical Cross-Linking for the Design of Materials for Tissue Engineering", Biomacromolecules, 2(2):430-441 (2001).
European Opposition dated Feb. 7, 2015 against European Patent EP 2066263.
European Search Report for EP Application No. 07809699.7, dated Jun. 12, 2004.
Hahn, et al., "Biocompatibility of Glow-Discharge-Polymerized Films and Vacuum-Deposited Parylene", J Applied Polymer Sci, 38:55-64 (1984).
Hahn, et al., "Glow Discharge Polymers as Coatings for Implanted Devices", ISA, pp. 109-111 (1981).
He, et al., "Assessment of Tissue Blood Flow Following Small Artery Welding with a Intraluminal Dissolvable Stent", Microsurgery, 19(3):148-152 (1999).
International Search Report for PCT/US2007/014331, dated Dec. 28, 2007.
Kelley, et al., "Totally Resorbable High-Strength Composite Material", Advances in Biomedical Polymers, 35:75-85 (1987).
Kubies, et al., "Microdomain Structure in polylactide-block-poly(ethylene oxide) copolymer films", Biomaterials, 21(5):529-536 (2000).
Kutryk, et al., "Coronary Stenting: Current Perspectives", a companion to the Handbook of Coronary Stents, pp. 1-16 (1999).
Martin, et al., "Enhancing the biological activity of immobilized osteopontin using a type-1 collagen affinity coating", J. Biomed. Mater Res, 70A:10-19 (2004).
Mauduit, et al., "Hydrolytic degradation of films prepared from blends of high and low molecular weight poly(DL-lactic acid)s", J. Biomed. Mater. Res., 30(2):201-207 (1996).
Middleton, et al., "Synthetic biodegradable polymers as orthopedic devices", Biomaterials, 21(23):2335-2346 (2000).
Muller, et al., "Advances in Coronary Angioplasty: Endovascular Stents", Coron. Arter. Dis., 1(4):438-448 (1990).
Nichols, et al., "Electrical Insulation of Implantable Devices by Composite Polymer Coatings", ISA Transactions, 26(4):15-18 (1987).
Peuster, et al., "A novel approach to temporary stenting: degradable cardiovascular stents produced from corrodible metal-results 6-18 months after implantation into New Zealand white rabbits", Heart, 86(5):563-569 (2001).
Pietrzak, et al., "Bioabsorbable Fixation Devices: Status for the Craniomaxillofacial Surgeon", J. Craniofaxial Surg., 8(2):92-96 (1997).
Pietrzak, "Bioresorbable implants—practical considerations", Bone, 19(1):109S-119S (Supplement Jul. 1996).
Redman, "Clinical Experience with Vasovasostomy Utilizing Absorbable Intravasal Stent", Urology, 20(1):59-61 (1982).
Rust, et al., "The Effect of Absorbable Stenting on Postoperative Stenosis of the Surgically Enlarged Maxillary Sinus Ostia in a Rabbit Animal Model", Archives of Otolaryngology, 122(12):1395-1397 (1996).
Schatz, "A View of Vascular Stants", Circulation, 79(2):445-457 (1989).
Schmidt, et al., "Long-Term Implants of Parylene-C Coated Microelectrodes", Med & Biol Eng & Comp, 26(1):96-101 (1988).
Spagnuolo, et al., "Gas 1 is induced by VE-cadherin and vascular endothelial growth factor and inhibits endothelial cell apoptosis", Blood, 103(8):3005-3012 (2004).
Tamai, et al., "Initial and 6-Month Results of Biodegradable Poly-I-Lactic Acid Coronary Stents in Humans", Circulation, 102(4):399-404 (2000).
Tsuji, et al., "Biodegradable Polymeric Stents", Current Interventional Cardiology Reports, 3(1):10-17 (2001).
Völkel, et al., "Targeting of immunoliposomes to endothelial cells using a single-chain Fv fragment directed against human endoglin(CD105)", Biochimica et Biophysica Acta, 1663(1-2):158-166 (2004).
Von Recum, et al., "Degradation of polydispersed poly(L-lactic acid) to modulate lactic acid release", Biomaterials, 16(6):441-445 (1995).
Yau, et al., "Modern Size-Exclusion Liquid Chromatography", Wiley-Interscience Publication, Table of Contents IX-XV (1979).

\* cited by examiner

PROCESS FOR LOADING A STENT ONTO A STENT DELIVERY SYSTEM

CROSS-REFERENCE TO RELATED APPLICATIONS

This application is a continuation of U.S. patent application Ser. No. 11/064,692, filed Feb. 23, 2005, now U.S. Pat. No. 9,295,570, which is a divisional of U.S. patent application Ser. No. 09/957,216, filed Sep. 19, 2001, now U.S. Pat. No. 6,863,683 issued Mar. 8, 2005, the contents of each of which are incorporated by reference in their entireties, and to each of which priority is claimed.

FIELD OF THE INVENTION

The present invention relates to a cold-molding process for loading a stent onto a stent delivery system. More specifically, the present invention relates to a method of loading a stent onto a balloon having creases that extend non-uniformly into the interstices of the stent without the use of a heating step.

BACKGROUND OF THE INVENTION

A stent is commonly used alone or in conjunction with angioplasty to ensure patency through a patient's stenosed vessel. Stents overcome the natural tendency of the vessel walls of some patients to restenose after angioplasty. A stent is typically inserted into a vessel, positioned across a lesion, and then expanded to create or maintain a passageway through the vessel, thereby restoring near-normal blood flow through the vessel.

A variety of stents are known in the art, including self-expandable and expandable stents, as well as wire braid stents. One such stent is described, for example, in U.S. Pat. No. 4,733,665 to Palmaz. Expandable stents are typically delivered to treatment sites on delivery devices, such as balloon catheters or other expandable devices. Balloon catheters may comprise a balloon having a collapsed delivery configuration with wings that are wrapped and folded about the catheter. An expandable stent is then disposed in a collapsed delivery configuration about the balloon by compressing the stent onto the balloon. The stent and balloon assembly may then be delivered, using well-known percutaneous techniques, to a treatment site within the patient's vasculature, for example, within the patient's coronary arteries. Once the stent is positioned across a lesion at the treatment site, it is expanded to a deployed configuration by inflating the balloon. The stent contacts the vessel wall and maintains a path for blood flow through the vessel.

Significant difficulties have been encountered during stent delivery and deployment, including difficulty in maintaining the stent on the balloon and in achieving symmetrical expansion of the stent when deployed. Several techniques have been developed to more securely anchor the stent to the balloon and to ensure more symmetrical expansion. These include plastically deforming the stent so that it is crimped onto the balloon, and sizing the stent such that its internal diameter provides an interference fit with the outside diameter of the balloon catheter. Such techniques have several drawbacks, including less than optimal securement of the stent to the balloon. Consequently, the stent may become prematurely dislodged from the balloon during advancement of the stent delivery system to the treatment site.

Stent delivery systems utilizing a removable sheath disposed over the exterior surface of the stent, which is removed once the stent is positioned at the treatment site, have also been proposed, for example, in U.S. Pat. No. 5,690,644 to Yurek et al. Such systems may be used with or without retainer rings and are intended to protect the stent during delivery and to provide a smooth surface for easier passage through the patient's vasculature. However, the exterior sheath increases the crossing profile of the delivery system while decreasing flexibility, thereby decreasing the ability of the device to track through narrowed and tortuous anatomy.

U.S. Pat. No. 6,106,530 to Harada describes a stent delivery device comprising a balloon catheter having stoppers disposed proximal and distal of a balloon on to which a stent is affixed for delivery. The stoppers are separate from the balloon and maintain the stent's position in relation to the balloon during delivery. As with the removable sheaths discussed previously, the stoppers are expected to increase delivery profile and decrease flexibility of the stent/balloon system.

U.S. Pat. No. 6,110,180 to Foreman et al. provides a catheter with a balloon having pre-formed, outwardly-extending protrusions on the exterior of the balloon. A stent may be crimped onto the balloon such that the protrusions extend into the gaps of the stent, thereby securing the stent about the balloon for delivery. A drawback to this device is the added complexity involved in manufacturing a balloon with pre-formed protrusions. Additionally, if the protrusions are not formed integrally with the balloon, there is a risk that one or more of the protrusions may detach during deployment of the stent. The protrusions may also reduce flexibility in the delivery configuration, thereby reducing ability to track through tortuous anatomy.

U.S. Pat. No. 5,836,965 to Jendersee et al. describes a hot-molding process for encapsulating a stent on a delivery system. Encapsulation entails placement of the stent over a balloon, placement of a sheath over the stent on the balloon, and heating the pressurized balloon to cause it to expand around the stent within the sheath. The assembly is then cooled while under pressure to cause the balloon to adhere to the stent and to set the shape of the expanded balloon, thereby providing substantially uniform contact between the balloon and the stent. This method also provides a substantially uniform delivery profile along the surface of the encapsulated balloon/stent assembly.

A significant drawback of Jendersee's encapsulation method is the need to heat the balloon in order to achieve encapsulation. Such heating while under pressure may lead to localized plastic flows resulting in inhomogeneities along the length of the balloon including, for example, varying wall thickness. Varying wall thickness may, in turn, yield areas of decreased strength that are susceptible to rupture upon inflation of the balloon during deployment of the stent. Additionally, heating and cooling increases the complexity, time, and cost associated with affixing the stent to the balloon.

U.S. Pat. No. 5,976,181 to Whelan et al. provides an alternative technique for stent fixation involving the use of solvents to soften the balloon material. In this method, the stent is disposed over an evacuated and wrapped balloon while in its compact delivery configuration. A rigid tube is then placed over the stent and balloon assembly, and the balloon is pressurized while the balloon is softened by application of a solvent and/or heating. The rigid tube prevents the stent from expanding but allows the balloon to deform so that its surface projects through either or both of the interstices and ends of the stent. Softening under pressure molds the balloon material such that it takes a permanent set into the stent. Once pressure is removed, the stent is interlocked with the surface of the balloon, providing substantially uniform contact between the balloon and the stent and a substantially uniform delivery profile.

As with the technique in the Jendersee patent, the technique in the Whelan patent has several drawbacks. Chemically softening the balloon material under pressure is expected to introduce inhomogeneities along the length of the balloon, such as varying wall thickness, which again may lead to failure of the balloon. Additionally, chemical alteration of the balloon, via application of a solvent to the surface of the balloon, may unpredictably degrade the mechanical characteristics of the balloon, thereby making accurate and controlled deployment of a stent difficult. Softening also adds cost, complexity, and time to the manufacturing process.

In view of the drawbacks associated with previously known methods and apparatus for loading a stent onto a stent delivery system, it would be desirable to provide methods and apparatus that overcome those drawbacks.

It would be desirable to provide methods and apparatus for loading a stent onto a stent delivery system that enhance positional stability of the stent during delivery.

It would further be desirable to provide methods and apparatus for loading a stent onto a stent delivery system wherein the delivery system comprises a crossing profile and flexibility suitable for use in tortuous and narrowed anatomy.

It would still further be desirable to provide methods and apparatus for loading a stent onto a stent delivery system that provide a substantially symmetrical expansion of the stent at deployment.

It would also be desirable to provide methods and apparatus for loading a stent onto a stent delivery system that do not unpredictably modify the mechanical characteristics of the balloon during fixation of the stent to the balloon.

SUMMARY OF THE INVENTION

In view of the foregoing, it is an object of the present invention to provide methods and apparatus for loading a stent onto a stent delivery system and deployment that overcome drawbacks associated with previously known methods and apparatus.

It is an object to provide methods and apparatus for loading a stent onto a stent delivery system that enhance positional stability of the stent during delivery.

It is an object to provide methods and apparatus for loading a stent onto a stent delivery system wherein the delivery system comprises a crossing profile and flexibility suitable for use in tortuous and narrowed anatomy.

It is also an object to provide methods and apparatus for loading a stent onto a stent delivery system that provide a substantially symmetrical expansion of the stent at deployment.

It is an object to provide methods and apparatus for loading a stent onto a stent delivery system that do not unpredictably modify the mechanical characteristics of the balloon during fixation of the stent to the balloon.

These and other objects of the present invention are achieved by providing methods and apparatus for cold-molding a stent to the balloon of a stent delivery system so that the balloon extends non-uniformly into the interstices of the stent. In a preferred embodiment, the stent is a balloon expandable stent and is manufactured in a fully-expanded state or in an intermediate-expanded state (i.e., having a diameter smaller than its fully-expanded, deployed diameter, but larger than its compressed delivery diameter).

The stent is disposed on the balloon of a delivery catheter, and the balloon and stent are placed within an elastic crimping tube. The balloon/stent/crimping tube assembly is then placed in a crimping tool, and the balloon is inflated, preferably only partially. The crimping tool is actuated to compress the stent on the outside of the partially inflated balloon and to cause creases of the balloon to extend non-uniformly into the interstices of the stent. Crimping occurs at a substantially constant temperature, without the use of chemicals. The balloon is then deflated, and the elastic crimping tube is removed.

Optionally, pillows or bumpers may be formed in the proximal and/or distal regions of the balloon during crimping that, in conjunction with the non-uniform creases of the balloon, prevent longitudinal movement of the stent with respect to the balloon during intravascular delivery.

Furthermore, one or more additional, secondary crimping steps may be performed to achieve a smoother delivery profile, in which a semi-rigid crimping tube is disposed over the stent delivery system, and the assembly is again disposed within the crimping tool. During secondary crimping, the crimping tool is actuated to further compress the stent onto the unpressurized balloon. Secondary-crimping may alternatively be performed with the balloon partially or completely pressurized/inflated.

Apparatus of the present invention may be used with a variety of prior art stents, such as balloon expandable stents, and may include tubular slotted stents, connected stents, articulated stents, multiple connected or non-connected stents, and bi-stable stents. In addition to methods of production, methods of using the apparatus of the present invention are provided.

BRIEF DESCRIPTION OF THE DRAWINGS

Further features of the invention, its nature and various advantages will be more apparent from the following detailed description of the preferred embodiments, taken in conjunction with the accompanying drawings, in which like reference numerals refer to like parts throughout, and in which.

DETAILED DESCRIPTION OF THE INVENTION

The present invention comprises methods and apparatus for cold-molding a stent onto a stent delivery system. More specifically, the present invention provides methods and apparatus for obtaining a balloon having creases that extend non-uniformly into the interstices of a stent loaded onto the exterior of the balloon, without the use of a heating or chemical process.

Figure 1A:
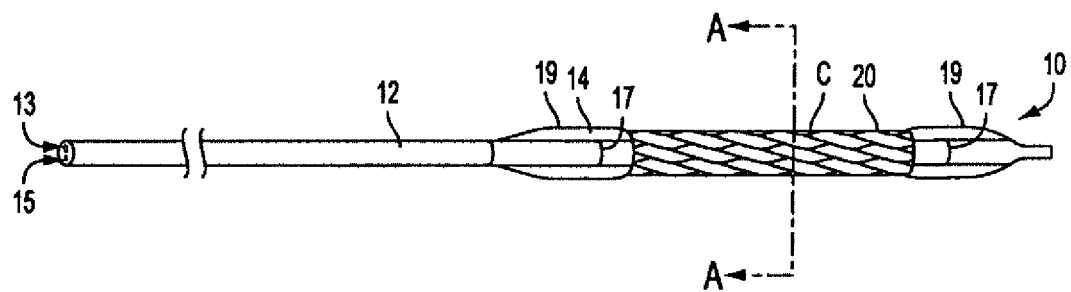
FIGS. 1A-1C are, respectively, a side view of a stent delivery system in accordance with the present invention, a cross-sectional view of the system along section line A-A in FIG. 1A, and a detail view of the balloon of the system non-uniformly extending within the interstices of the stent.
Figure 1B:
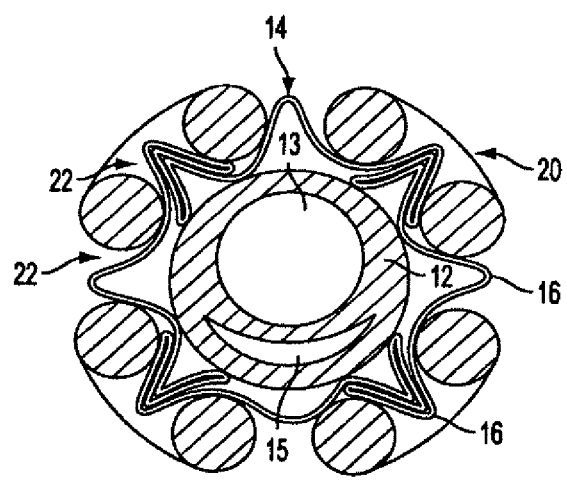
Figure 1C:
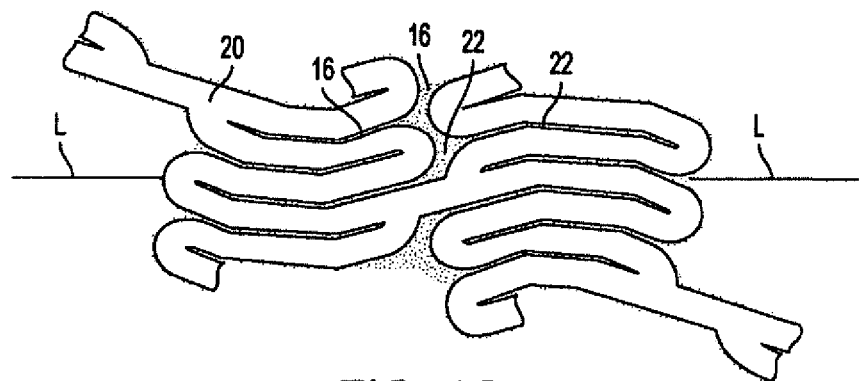

With reference to FIG. 1, apparatus in accordance with the present invention is described. As seen in FIG. 1A, stent delivery system 10, illustratively shown in a collapsed delivery configuration, comprises balloon expandable stent 20 loaded on balloon 14 of delivery catheter 12. Stent 20 comprises an illustrative balloon expandable stent and may be replaced with other stents known in the art. As seen in FIGS. 1B and 1C, balloon 14 has creases 16 that extend non-uniformly into interstices 22 of stent 20.

In FIG. 1B, creases 16 are shown with varying slope and height about the circumference of stent delivery system 10. FIG. 1C depicts creases 16 as shaded areas and illustrates that creases 16 extend along the length of stent 20 within interstices 22. Line L indicates the longitudinal axis of stent 20 in FIG. 1C. It should be understood that creases 16 typically do not extend within every interstice 22 of stent 20.

Delivery catheter 12 preferably includes markers 17 disposed distal of and proximal to stent 20 that facilitate placement of stent 20 on balloon 14, and that facilitate positioning of stent delivery system 10 at a treatment site within a patient's vasculature. Markers 17 are preferably radiopaque and fabricated from a radiopaque material, such as platinum or gold. Catheter 12 preferably also comprises guide wire lumen 13 and inflation lumen 15, which is coupled to balloon 14. As described hereinbelow, during the cold-molding process of the present invention, proximal and/or distal pillows 19 optionally may be formed in balloon 14 during pressurized crimping. As with creases 16, pillows 19 act to reduce or prevent longitudinal movement of the stent on the balloon during intravascular delivery.

Balloon 14 is expandable by injection of a suitable medium, such as air or saline, via inflation lumen 15. Balloon 14 preferably expands stent 20 to a deployed configuration under application of pressure in the range of about 6-9 atm. Additionally, balloon 14 preferably has a rated burst pressure above 10 atm, and even more preferably between about 12-14 atm. Balloon 14 may be fabricated from a variety of materials, including Nylon, polyethylene terephalate, polyethylene, and polyether/polyamide block copolymers, such as PEBAX.

Additionally, balloon 14 may be fabricated from an elastomeric polyester block copolymer having an aromatic polyester hard segment and an aliphatic polyester soft segment, such as "Pelprene," which is marketed by the Toyobo Corporation of Osaka, Japan. Balloon 14 also may be fabricated from a copolymer having a polybutylene terephalate hard segment and a long chain of polyether glycol soft segment, such as "Hytrel" from the DuPont Corporation of Wilmington, Del.

Illustrative stent 20 may be fabricated from a variety of materials, including polymers and metals, and may comprise any of a variety of prior art stents, such as balloon expandable stents, including tubular slotted stents, connected stents, articulated stents, multiple connected or non-connected stents, and bi-stable stents. Stent 20 also may include external coating C configured to retard restenosis or thrombus formation in the vessel region surrounding the stent. Alternatively, coating C—may—deliver therapeutic agents into-the-patient's blood stream or vessel wall.

Figure 2:
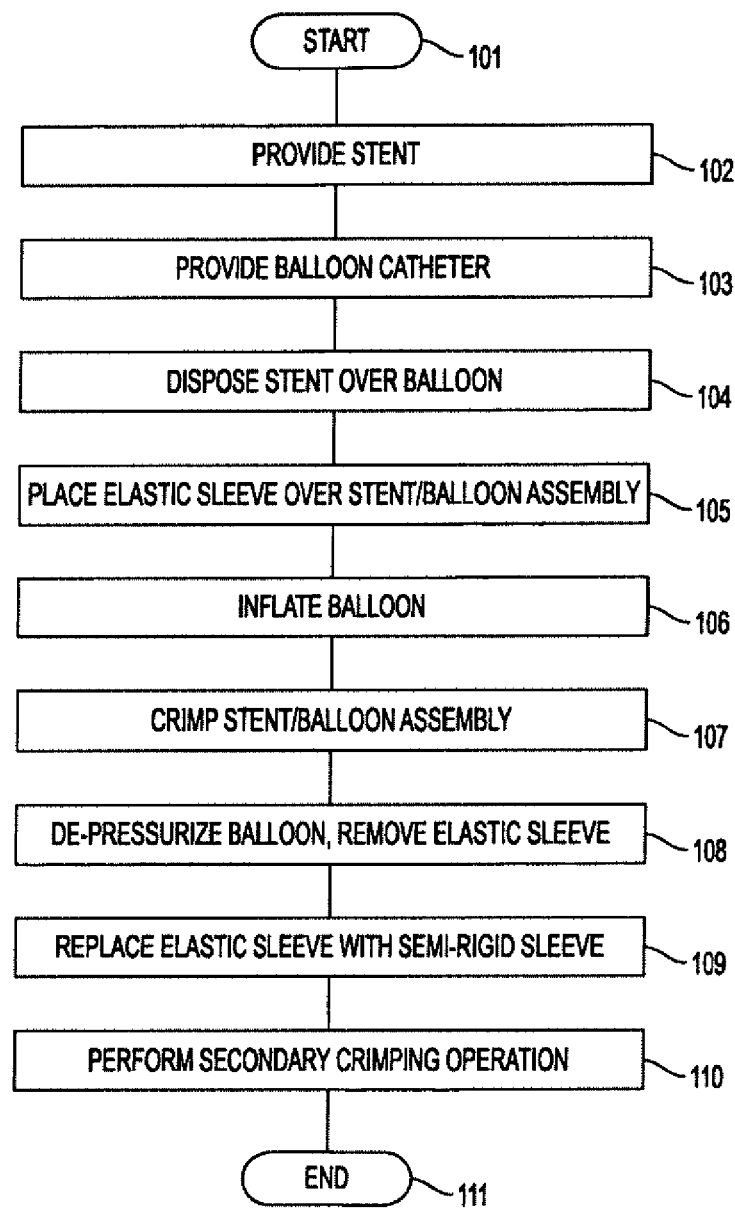
FIG. 2 is a flow chart showing the steps of the cold-molding process of the present invention.

Referring now to FIGS. 2-8, a method of producing stent delivery system 10 is described. FIG. 2 provides an overview of the cold-molding process of the present invention, while FIGS. 3-8 provide detailed views of these process steps.

As depicted in FIG. 2, the cold-molding process of the present invention involves steps of: obtaining a stent, step 102; obtaining a balloon catheter, step 103; disposing the stent on the balloon of the balloon catheter, step 104; and disposing an elastic crimping sleeve over the stent and balloon, step 105. In accordance with the method of the present invention, the balloon is then inflated—preferably only partially—with an inflatable medium, such as air, at step 106. The sleeve/stent/balloon assembly is then crimped within a crimping tool that compresses the stent onto the balloon, step 107, while the balloon is pressurized.

As described hereinbelow, this step causes the balloon to bulge into the interstices of the stent, and in addition, to form pillows 19, proximal of, and distal to, the ends of the stent to retain the stent in place during transluminal delivery. At step 108, the balloon is depressurized, and the elastic sleeve is removed to complete the stent loading process.

If desired, a semi-rigid sleeve optionally may be disposed over the stent/balloon assembly, and one or more additional crimping steps may be performed, steps 109 and 110 of FIG. 2.

Figure 3A:
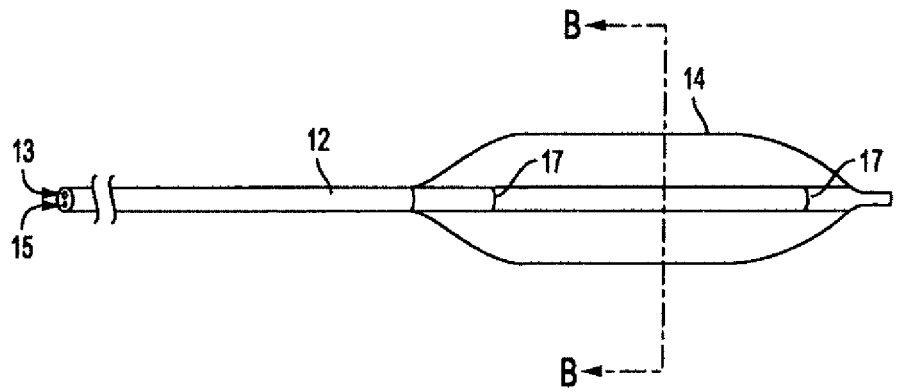
FIGS. 3A-3C are, respectively, a side view of the distal end of the delivery catheter of the system of FIG. 1 in an expanded configuration, and cross-sectional views of the catheter along section line B—B in FIG. 3A, showing the balloon evacuated to form radially extended wings and in a contracted configuration with the radially extended wings wrapped about the catheter.
Figure 3B:
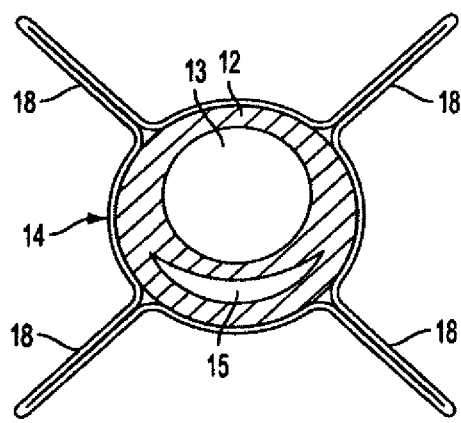
Figure 3C:
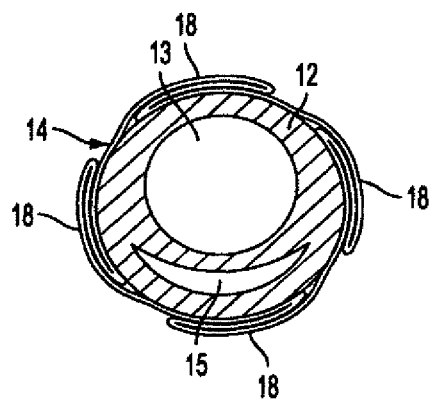

Referring now to FIGS. 3-8, additional details of a preferred embodiment of the process of the present invention are illustrated and described. In FIG. 3, balloon 14 of delivery catheter 12—preferably is folded prior to placement of stent 20 about balloon 14. Balloon 14 is first expanded, as in FIG. 3A, and then evacuated to form radially extended wings 18, as seen in FIG. 3B. Balloon 14 is illustratively depicted with four wings 18, but it should be understood that any number of wings may be provided, for example, two, three or five wings. In FIG. 3C, wings 18 are wrapped about the shaft of delivery catheter 12 to dispose catheter 12 in a contracted configuration. It should be understood that balloon 14 may alternatively be folded and/or disposed in a collapsed delivery configuration by other techniques, for example, with techniques that do not utilize wings.

Figure 4A:
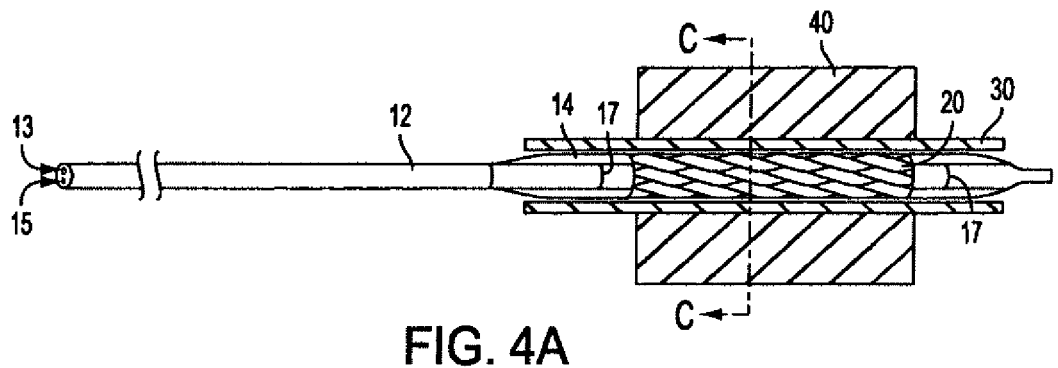
FIGS. 4A-4C are, respectively, a side view, partially in section, of the wrapped delivery catheter of FIG. 3C having the stent of FIG. 1 and an elastic crimping tube disposed thereover, the entire assembly disposed within a crimping tool; a cross-sectional view of the same along section line C-C in FIG. 4A; and a detail view of the expandable structure of the stent.

With reference to FIG. 4, stent 20 and elastic crimping tube 30 are disposed about balloon 14, preferably with stent 20 positioned between markers 17 of delivery catheter 12 (steps 102-105, FIG. 2). The balloon/stent/crimping tube assembly is inserted within crimping tool 40, as seen in FIG. 4A. Crimping tool 40 is preferably positioned between markers 17 to facilitate formation of optional pillows 19 during pressurization of balloon 14. Crimping tool 40 may be any of a variety of crimping tools known in the art. An illustrative crimping tool is described, for example, in U.S. Pat. No. 6,082,990 to Jackson et al., which is incorporated herein by reference.

Figure 4B:
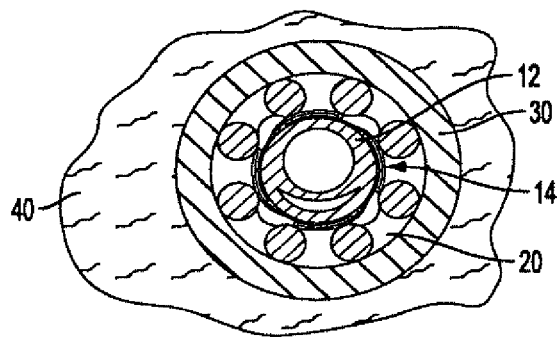

Referring to FIG. 4B, stent 20 may be directly placed about balloon 14, and elastic crimping tube 30 then may be loaded over the stent/balloon assembly. Alternatively, stent 20 may be placed within elastic crimping tube 30, and then the stent/tube assembly disposed surrounding balloon 14. As yet another alternative, crimping tube 30, or crimping tube 30 and stent 20, may be positioned within crimping tool 40; then, balloon 14, with or without stent 20 loaded thereon, may be positioned within crimping tool 40.

Figure 4C:
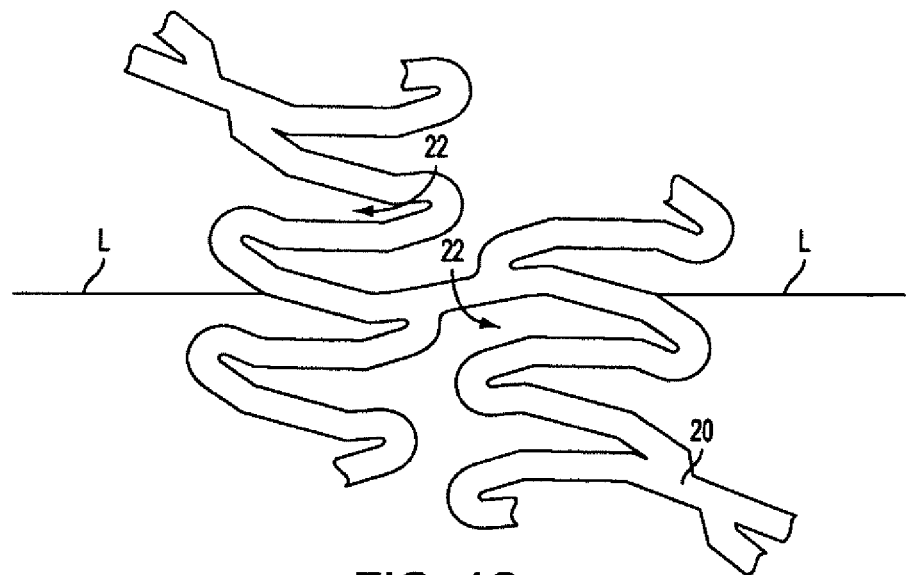

As depicted in FIG. 4C, stent 20 preferably is manufactured in an intermediate-expanded state having a diameter smaller than its expanded deployed diameter, but larger than its compressed delivery diameter, thereby facilitating positioning of stent 20 about balloon 14. When stent 20 is initially disposed surrounding balloon 14, the balloon does not substantially extend into interstices 22 of stent 20. It should be understood that stent 20 alternatively may be manufactured in a fully-expanded state.

Figure 5A:
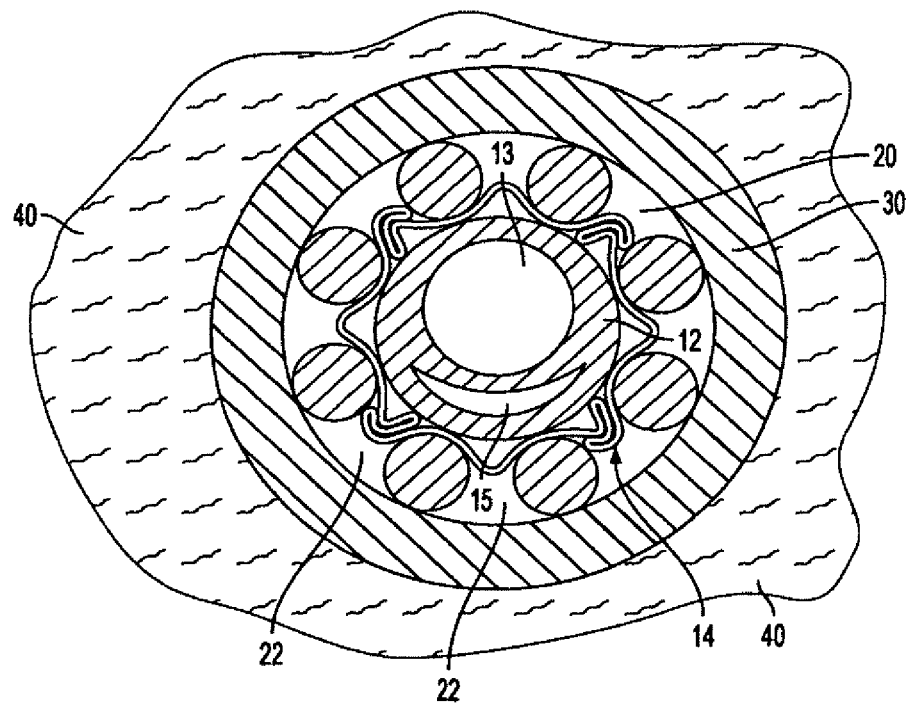
FIGS. 5A and 5B are, respectively, a cross-sectional view along section line C-C in FIG. 4A of the apparatus upon pressurization of the balloon, and a detail view of the expandable structure of the stent.
Figure 5B:
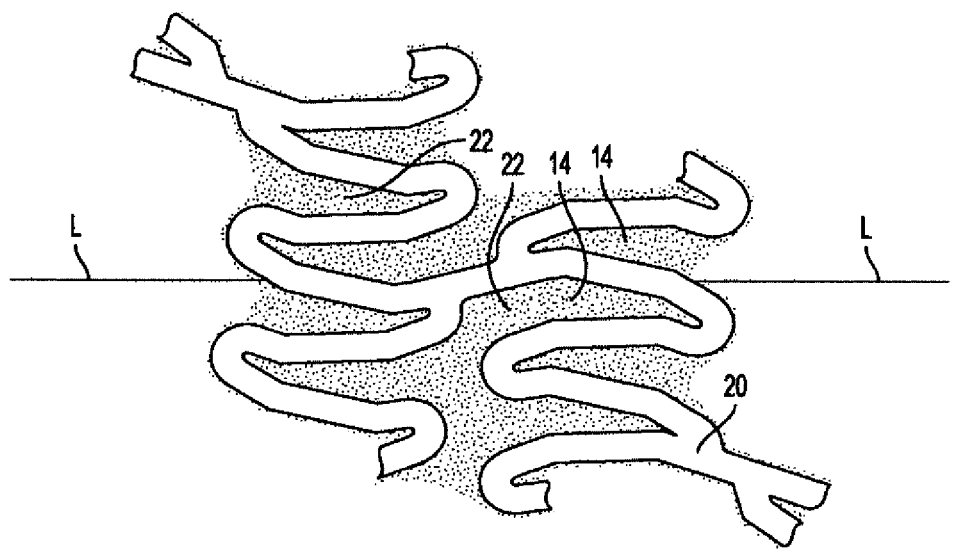

In FIG. 5, once stent 20 and crimping tube 30 are disposed about balloon 14 of delivery catheter 12, and once the entire assembly is disposed within crimping tool 40, balloon 14 is pressurized, for example, via an inflation medium delivered through inflation lumen 15 of catheter 12 (step 106, FIG. 2). Pressure application causes balloon 14 to enter a portion of interstices 22 of stent 20 in a non-uniform manner, as seen in the cross section of FIG. 5A and in the detail view of FIG. 5B. Crimping tube 30 and crimping tool 40 prevent expansion of stent 20 during partial or complete pressurization of balloon 14, as depicted in FIG. 5A.

The inflation medium is preferably delivered at a pressure in the range of about 6-8 atm. This pressure range is below the preferred rated burst pressure of balloon 14, which is above 10 atm, and even more preferably between about 12-14 atm, and thus ensures that the balloon does not puncture. The elasticity of crimping tube 30 allows the tube to expand slightly upon application of pressure, and to contract slightly during crimping. Tube 30 may be fabricated from any suitable—elastic material, for example, a polymer, such as PEBAX. Elastic crimping tube 30 preferably has a hardness of between about 30 and 40 Shore Hardness, and more preferably a hardness of about 35 Shore Hardness.

Figure 6:
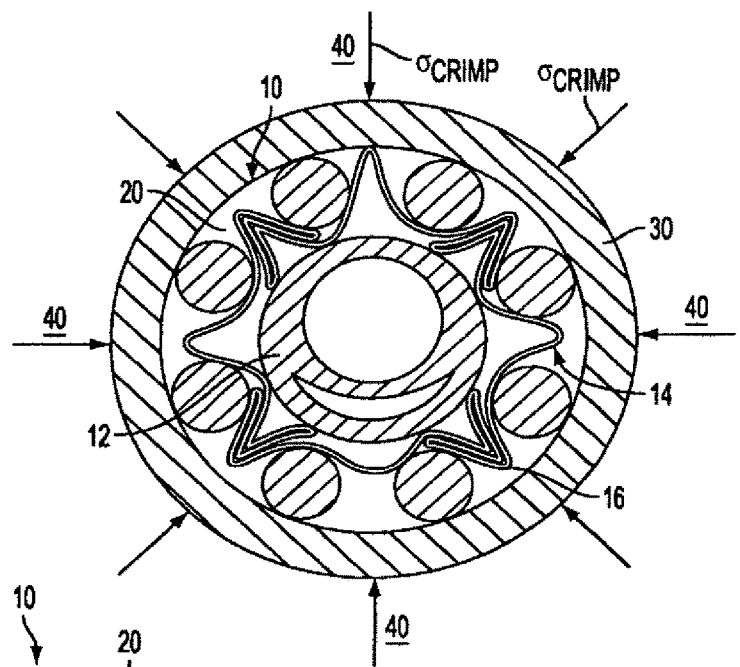
FIG. 6 is a cross-sectional view along section line C-c in FIG. 4A during crimping after pressure has been removed.

With reference to FIG. 6, in conjunction with FIG. 4A, crimping tool 40 is actuated to crimp stent 20 onto balloon 14 (step 107, FIG. 2). Crimping tool 40 applies an inwardly-directed stress, $\sigma_{crimp}$, to the assembly. Initially, balloon 14 is still pressurized. Stent 20 is compressed onto the outside of balloon 14, causing the balloon to further bulge non-uniformly into interstices 22 of the stent. Crimping preferably proceeds along the length of the balloon/stent/tube assembly all at once but may alternatively proceed in sections, so that the assembly is gradually crimped along its length.

Balloon 14 is then depressurized, allowing crimping tool 40 to further compress stent 20 onto balloon 14, as seen in FIG. 6 (step 108, FIG. 2), which forms creases 16 of balloon 14 that extend non-uniformly within interstices 22 of the stent. Creases 16 are most clearly seen in FIGS. 1B and 1C. Optional pillows 19 of stent delivery system 10 are also formed. Since many prior art crimping tools 40 apply an inwardly-directed stress, $\sigma_{crimp}$, that is not uniform about the radius of balloon 14, elastic crimping tube 30 acts to more uniformly distribute the stress about the circumference of the balloon/stent assembly.

Stent delivery system 10 is removed from elastic crimping tube 30 and crimping tool 40 (step 108, FIG. 2). Stent delivery system 10 has a low-profile delivery configuration adapted for percutaneous delivery within a patient's vasculature, as described hereinbelow with respect to FIG. 9. Creases 16, as well as pillows 19, secure stent 20 to balloon 14 between markers 17 of delivery catheter 12.

In contrast to prior art techniques described hereinabove, crimping in accordance with the present invention occurs at a substantially constant temperature, without the use of chemicals. In the context of the present invention, substantially constant temperature during crimping should be understood to include minor fluctuations in the actual temperature due to frictional losses, etc.

Importantly, the system of the present invention is not actively heated to thermally remodel the balloon, as described in U.S. Pat. No. 5,836,965 to Jendersee et al. Likewise, no solvents are added to soften and mold the balloon, as described in U.S. Pat. No. 5,976,181 to Whelan et al. As described previously, both heating and solvents have significant potential drawbacks, including inhomogeneities along the length of the balloon, such as varying wall thickness. Varying wall thickness may yield areas of decreased strength that are susceptible to rupture upon inflation of the balloon during deployment of the stent. Additionally, heating and cooling, as well as addition of solvents, increases the complexity, time, and cost associated with affixing the stent to the balloon.

Theoretical bounds for the radial stress that may be applied to balloon 14 during crimping, while the balloon is pressurized, may be estimated by modeling balloon 14 as an idealized tube and assuming crimping tool 40 applies an evenly distributed, inwardly-directed radial stress, $\sigma_{crimp}$. Stent 20 and elastic crimping tool 30, meanwhile, theoretically resist the crimping stress with an outwardly-directed radial stress, $\sigma_{resistance}$. Thus, the composite inwardly-directed radial stress, $\sigma_{in}$, applied to balloon 14 may be idealized as:

$$\sigma_{in} = \sigma_{crimp} - \sigma_{resistance} \quad (1)$$

Pressurization/inflation of balloon 14 similarly may be modeled as an evenly distributed, outwardly-directed radial stress, $\sigma_o$, and it may be assumed that the rated burst pressure of balloon 14 is the yield stress of the balloon, $\sigma_y$. A stress balance provides:

$$\sigma_{in} - \sigma_{out} < \sigma_y \quad (2)$$

Thus, a theoretical upper bound for the radial stress, $\sigma_y$ that may be applied to balloon 14 is:

$$\sigma_{in} < \sigma_y + \sigma_{out} \quad (3)$$

A theoretical lower bound for $\sigma_y$ in also may be found by observing that, in order to compress stent 20 onto the exterior of balloon 14, crimping tool 40 must apply a radial stress, $\sigma_{crimp}$, that is greater than the net stress provided by resistance of stent 20 and crimping tube 30, $\sigma_{resistance}$, and by the inflation of balloon 14, $\sigma_{out}$:

$$\sigma_{crimp} > \sigma_{out} + \sigma_{resistance} \quad (4)$$

Combining Equation (1) and (4) provides a lower bound for $\sigma_{in}$:

$$\sigma_{in} > \sigma_{out} \quad (5)$$

Finally, combining Equations (3) and (5) provides a range for $\sigma_{in}$:

$$\sigma_{out} < \sigma_{in} < \sigma_y + \sigma_{out} \quad (6)$$

As an example, assuming a burst pressure, $\sigma_y$, of 12 atm and a balloon pressurization, $\sigma_{out}$, of 8 atm, the balloon will theoretically withstand an inwardly-directed stress, $\sigma_{in}$, of up to 20 atm. Furthermore, in order to ensure that stent 20 is crimped onto balloon 14, $\sigma_{in}$ must be greater than 8 atm. Thus, the inwardly-directed radial stress must be between 8 and 20 atm. Assuming, for example, a resistance stress, $\sigma_{resistance}$, of 2 atm, crimping tool 40 must apply a crimping stress, $\sigma_{crimp}$, between 10 and 22 atm. As one of ordinary skill will readily understand, the actual radial stress applied should be further optimized within this range to provide a safety factor, optimal crimping, etc. Since balloon 14 is not in reality an idealized tube, stresses applied to the balloon will have a longitudinal component in addition to the radial component, which may be, for example, accounted for in the safety factor.

Figure 7:
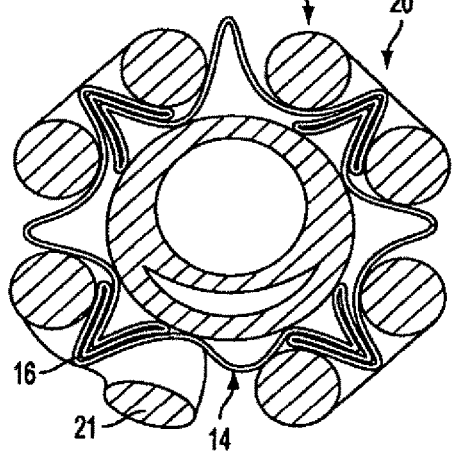
FIG. 7 is a cross-sectional view along section line C-C in FIG. 4A of a possible configuration of the stent delivery system after crimping and removal of the elastic crimping tube.

With reference now to FIG. 7, a possible configuration of the stent delivery system after crimping and removal of elastic crimping tube 30 is described. One or more struts 21 of stent 20 may be incompletely compressed against balloon 14. Such a strut may potentially snag against the patient's vasculature during delivery, and thereby prevent positioning of stent delivery system 10 at a treatment site. Additionally, pressurized crimping may result in a delivery profile for delivery system 10 that is more polygonal than cylindrical, thereby applying undesirable stresses on the vessel wall during transluminal insertion. Accordingly, it may be desirable to perform an optional secondary crimping step after balloon 14 has been depressurized.

Figure 8:
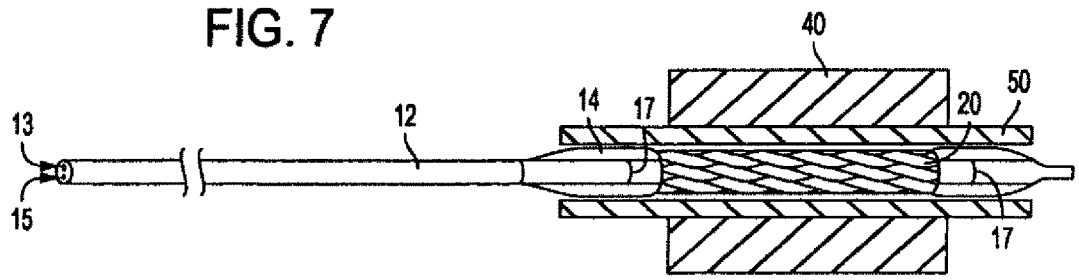
FIG. 8 is a side view, partially in section, of the stent delivery system disposed within a semi-rigid crimping tube and within the crimping tool for optional secondary crimping.

Referring to FIG. 8, in order to reduce the potential for incompletely compressed individual struts 21 of stent 20, and to provide a more uniform cylindrical delivery profile, one or more additional, secondary crimping steps may be performed on stent delivery system 10. In FIG. 8, stent delivery system 10 is disposed within semi-rigid crimping tube 50, which is disposed within crimping tool 40 (step 109, FIG. 2). Tube 50 may be fabricated from any suitable semi-rigid material. As with elastic crimping tube 30, semi-rigid crimping tube 50 preferably comprises a polymer, such as PEBAX. Semi-rigid crimping tube 50 preferably has a hardness of between about 50 and 60 Shore Hardness, and more preferably a hardness of about 55 Shore Hardness.

With stent delivery system 10 disposed within semi-rigid tube 50 and crimping tool 40, tool 40 is actuated to compress individual struts 21 against balloon 14 and to give delivery system 10 the substantially cylindrical delivery profile of FIG. 1B (step 110, FIG. 2). As with elastic crimping tube 30, semi-rigid tube 50 acts to evenly distribute crimping stresses applied by crimping tool 40 around the circumference of the stent/balloon assembly. Since balloon 14 is not pressurized, secondary crimping preferably proceeds in sections along the length of stent delivery system 10. However, as will be apparent to those of skill in the art, secondary crimping may proceed in one step. Optionally, balloon 14 may be pressurized during secondary crimping.

Referring now to FIG. 9, a method of using stent delivery system 10 of the present invention is described. Stent delivery system 10 is disposed in a contracted delivery configuration with stent 20 disposed over balloon 14 of delivery catheter 12. Creases 16 of balloon 14 non-uniformly extend within interstices 22 of stent 20. Creases 16, in conjunction with optional pillows 19, act to secure stent 20 to balloon 14. As seen in FIG. 9A, the distal end of catheter 12 is delivered to a target site T within a patient's vessel V using, for example, well-known percutaneous techniques. Target site T may, for example, comprise a stenosed region of vessel V. The radiopacity of markers 17 may facilitate positioning of system 10 at the target site. Alternatively, stent 20 or other portions of catheter 12 may be radiopaque to facilitate positioning.

Figure 9A:
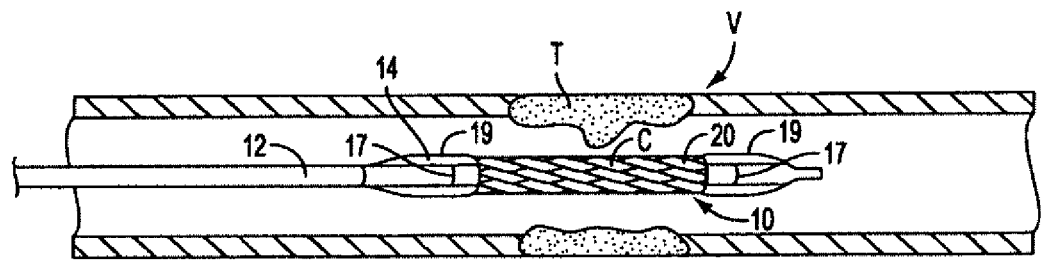
FIGS. 9A-9D are side views, partially in section, of the stent delivery system of FIG. 1 disposed within a patient's vasculature, depicting a method of using the apparatus in accordance with the present invention.
Figure 9B:
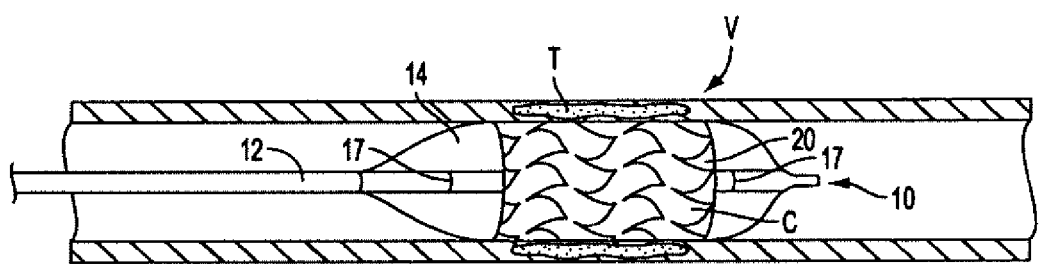
Figure 9C:
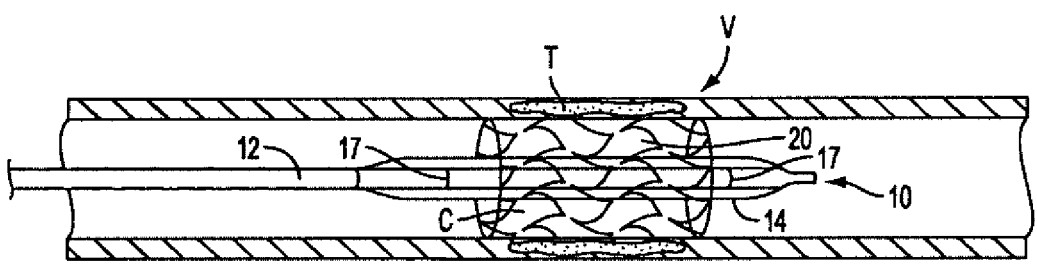
Figure 9D:
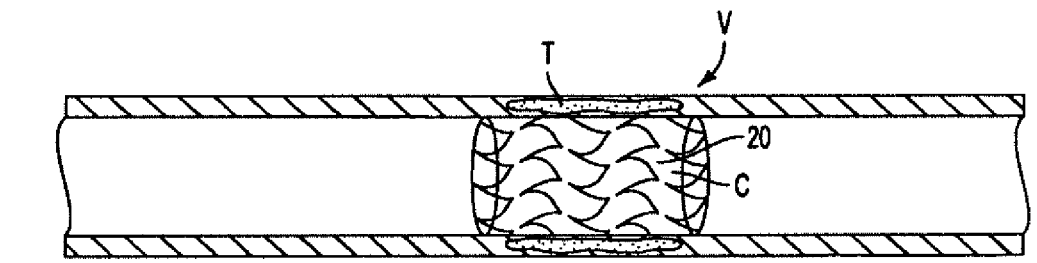

In FIG. 9B, balloon 14 is inflated, for example, via an inflation medium delivered through inflation lumen 15 of catheter 12. Stent 20 expands to the deployed configuration in which it contacts the wall of vessel V at target site T. Expansion of stent 20 opens interstices 22 of the stent and removes the non-uniform creases of balloon 14 from within the interstices. Additionally, stent 20 has a diameter in the deployed configuration that is larger than the diameter of optional pillows 19, thereby facilitating removal of stent 20 from delivery catheter 12. Balloon 14 is then deflated, as seen in FIG. 9C, and delivery catheter 12 is removed from vessel V, as seen in FIG. 9D.

Stent 20 remains in place within vessel V in the deployed configuration in order to reduce restenosis and recoil of the vessel. Stent 20 also may comprise external coating C configured to retard restenosis or thrombus formation around the stent. Alternatively, coating C may deliver therapeutic agents into the patient's blood stream or a portion of the vessel wall adjacent to the stent.

Although preferred illustrative embodiments of the present invention are described hereinabove, it will be evident to those skilled in the art that various changes and modifications may be made therein without departing from the invention.

For example, stent delivery system 10 may be produced without using elastic crimping tube 30. In this case, the stent/balloon assembly would be loaded directly into crimping tool 40, which would limit expansion of balloon 14 during pressurization. Likewise, semi-rigid crimping tube 50 may be eliminated from the secondary crimping procedure. If crimping tubes are not used, crimping tool 40 preferably applies an inwardly-directed stress that is substantially evenly distributed about the circumference of the stent/balloon assembly.

Additionally, balloon 14 may be depressurized prior to crimping stent 20 onto the balloon. This may be particularly beneficial when crimping long stents, for example, stents longer than about 50 mm. Pressurization of balloon 14 may cause the balloon to increase in longitudinal length. When crimping a long stent 20 onto a correspondingly long balloon 14, this increase in balloon length is expected to be more significant, for example, greater than about 1 mm.

If stent 20 is crimped onto balloon 14 while the balloon is pressured, significant stresses may be encountered along creases 16 after balloon 14 is depressurized, due to contraction of the balloon back to its shorter, un-inflated longitudinal length. These stresses may, in turn, lead to pinhole perforations of balloon 14. Thus, since pressurization of balloon 14 causes the balloon to extend at least partially within interstices 22 of stent 20 in a non-uniform manner, as seen in FIG. 5A, it is expected that crimping after depressurization will still establish creases 16 of stent delivery system 10, in accordance with the present invention. Obviously, crimping after depressurization may be done with stents 20 of any length, not just long stents.

It is intended in the appended claims to cover all such changes and modifications that fall within the true spirit and scope of the invention.

What is claimed is:

1. A stent delivery system having a contracted delivery configuration and an expanded deployed configuration, the stent delivery system comprising:

a stent having a plurality of expandable elements and a plurality of interstices disposed between adjacent expandable elements; and a delivery catheter having an inflatable balloon comprising creases extending non-uniformly within the interstices of the stent in the contracted delivery configuration, each crease defining a maximum radial height within a corresponding interstice, wherein the maximum radial heights of the creases vary.

2. The stent delivery system of claim 1, wherein the stent comprises a metal stent.

3. The stent delivery system of claim 1, wherein the stent comprises a polymer stent.

4. The stent delivery system of claim 1, wherein the stent comprises an external coating.

5. The stent delivery system of claim 1, wherein the creases include a folded first region having at least one fold of the balloon folded into at least an interstice and a second folded region having a least two folds of the balloon folded into at least a second interstice, wherein the creases are captured within the interstices to releasably affix the stent to the inflatable balloon.

6. The stent delivery system of claim 1, wherein the balloon has a working length and is free from heat-induced and solvent-induced inhomogeneities along the working length of the balloon.

7. The stent delivery system of claim 1, wherein the creases have varying slope about a circumference of the stent delivery system.

8. The stent delivery system of claim 1, wherein a first crease corresponding to a first interstice has a first maximum radial height greater than a radial midpoint of the first interstice and a second crease corresponding to a second interstice has a second maximum radial height less than a radial midpoint of the second interstice.

9. A method for stenting at a target site within a patient's vessel, the method comprising:

providing a stent delivery system comprising a stent having a plurality of expandable elements and a plurality of interstices disposed between adjacent expandable elements and a delivery catheter with an inflatable balloon having creases extending non-uniformly within the interstices of the stent, each crease defining a maximum radial height within a corresponding interstice, wherein the maximum radial heights of the creases vary;

percutaneously delivering the stent delivery system to the target site within the patient's vessel in the contracted delivery configuration; and expanding the stent delivery system to an expanded deployed configuration, wherein the balloon is inflated, the interstices of the stent open, and the stent engages the target site.

10. The method of claim 9, wherein the stent comprises a metal stent.

11. The method of claim 9, wherein the stent comprises a polymer stent.

12. The method of claim 9, wherein the stent comprises an external coating.

13. The method of claim 9, wherein the creases include a first folded region having at least one fold of the balloon folded into at least a first interstice and a second folded region having at least two folds of the balloon folded into at least a second interstice, and wherein the creases are captured within the interstices to releasably affix the stent to the inflatable balloon.

14. The method of claim 9, further comprising:

deflating the balloon; and removing the delivery catheter from the patient's vessel.

15. The method of claim 9, wherein the balloon has a working length and is free from heat-induced and solvent-induced inhomogeneities along the working length of the balloon.

16. The method of claim 9, wherein the creases have varying slope about a circumference of the stent delivery system.

17. The method of claim 9, wherein a first crease corresponding to a first interstice has a first maximum radial height greater than a radial midpoint of the first interstice and a second crease corresponding to a second interstice has a second maximum radial height less than a radial midpoint of the second interstice.

* * * * *